(12) United States Patent
Flach (10) Patent No.: US 11,931,503 B2
(45) Date of Patent: Mar. 19, 2024

(54) MOBILE NEGATIVE PRESSURE WOUND THERAPY DEVICE WITH REDUCED PUMP NOISE

(71) Applicant: Mölnlycke Health Care AB, Gothenburg (SE)

(72) Inventor: Niclas Flach, Alingsås (SE)

(73) Assignee: Mölnlycke Health Care AB, Gothenburg (SE)

( * ) Notice: Subject to any disclaimer, the term of this patent is extended or adjusted under 35 U.S.C. 154(b) by 0 days.

(21) Appl. No.: 17/998,816

(22) PCT Filed: May 24, 2021

(86) PCT No.: PCT/EP2021/063749
§ 371 (c)(1),
(2) Date: Nov. 15, 2022

(87) PCT Pub. No.: WO2021/239654
PCT Pub. Date: Dec. 2, 2021

(65) Prior Publication Data
US 2023/0211068 A1    Jul. 6, 2023

(30) Foreign Application Priority Data
May 25, 2020  (EP) .................................... 20176280

(51) Int. Cl.
*A61M 1/00*    (2006.01)
(52) U.S. Cl.
CPC .............. *A61M 1/964* (2021.05); *A61M 1/82* (2021.05); *A61M 2205/33* (2013.01); *A61M 2205/42* (2013.01); *A61M 2205/8206* (2013.01)
(58) Field of Classification Search
CPC .......... A61M 1/80; A61M 1/802; A61M 1/82; A61M 2205/42; A61M 1/74;
(Continued)

(56) References Cited

U.S. PATENT DOCUMENTS

2010/0049150 A1*  2/2010  Braga ................... A61M 1/784
                                                       604/313
2017/0049606 A1*  2/2017  Chen ........................ A61F 5/56
(Continued)

FOREIGN PATENT DOCUMENTS

WO    WO 2019/086341 A1    5/2019
WO    WO 2019/211732 A1    11/2019

OTHER PUBLICATIONS

International Search Report and Written Opinion dated Jul. 1, 2021 by the International Searching Authority for International Application No. PCT/EP2021/063749 filed on May 24, 2021 and published as WO 2021/239654 (Applicant—Molnlycke Health Care AB) (10 pages).

*Primary Examiner* — Leslie A Lopez
*Assistant Examiner* — Seth Han
(74) *Attorney, Agent, or Firm* — Ballard Spahr LLP (57) ABSTRACT

A mobile negative pressure wound therapy (NPWT) device is described having an inlet; a canister in fluid flow connection with the inlet; a pump having a pump casing with a pump inlet in fluid flow connection with the canister in the canister, and a pump outlet for output of air transported through the pump; an elastomeric jacket at least partly enclosing the pump, the elastomeric jacket being configured to define a flow channel having a first end arranged to receive air output by the pump outlet and a second end spaced apart from the first end for discharging the air output by the pump outlet following passage through the flow channel; a control unit for controlling operation of the mobile NPWT device; a battery arrangement for powering the mobile NPWT device; and a housing enclosing at least the pump, the elastomeric jacket, the control unit, and the battery arrangement.

14 Claims, 5 Drawing Sheets

(58) Field of Classification Search
CPC ............. A61M 2205/3344; A61M 1/73; F04B 39/0044; F04B 39/0027; F04B 39/0033; F04B 39/0038; F04B 43/0081; F04B 17/003; F04B 2201/0801; F04B 2201/0806; F04B 2203/0405; F04B 2203/00; F04B 2201/00; F04B 43/046; F04B 49/06

See application file for complete search history.

(56) References Cited

U.S. PATENT DOCUMENTS

| | | | |
|---|---|---|---|
| 2018/0135615 A1* | 5/2018 | Snyder | F04B 39/0027 |
| 2019/0365966 A1* | 12/2019 | Bächler | F04B 39/0044 |
| 2020/0108213 A1* | 4/2020 | Akao | A61M 15/06 |

* cited by examiner

MOBILE NEGATIVE PRESSURE WOUND THERAPY DEVICE WITH REDUCED PUMP NOISE

CROSS-REFERENCE TO RELATED APPLICATIONS

This application is a U.S. National Phase Application of International Application No. PCT/EP2021/063749, filed May 24, 2021, which claims priority to European Patent Application No. 20176280.4, filed May 25, 2020, each of which is hereby incorporated by reference in its respective entirety.

FIELD OF THE INVENTION

The present invention relates to a mobile negative pressure wound therapy (NPWT) device, and to an NPWT system comprising such a mobile NPWT device.

BACKGROUND OF THE INVENTION

Negative pressure wound therapy (NPWT) is a technique that promotes healing of e.g. surgical, acute and chronic wounds by the application of a negative (that is, sub-atmospheric) pressure to the wound, using a negative pressure pump. The NPWT technique permits less outside disturbance of the wound as well as provides for transportation of excess fluids away from the wound site. Generally, the NPWT technique has until now mainly been applied in a hospital environment. However, recent product development allows the technique to be used in a home environment.

In order to make it easier and more comfortable for a user to benefit from NPWT, mobile NPWT devices have been developed. For such an NPWT device to be truly mobile, it needs to be compact and light. This requirement for a small and light NPWT device makes it challenging to keep the sound emitted by the mobile NPWT device sufficiently unobtrusive to the user of the mobile NPWT device.

SUMMARY

It is an object of the present invention to provide an improved mobile NPWT device, in particular a more silent mobile NPWT device.

According to the present invention, it is therefore provided a mobile negative pressure wound therapy (NPWT) device, comprising: an inlet to be in fluid flow connection with a wound site; a canister in fluid flow connection with the inlet for collection of liquid from the wound site; a pump having a pump casing with a pump inlet in fluid flow connection with the canister for establishing a negative pressure in the canister, and a pump outlet for output of air transported through the pump; an elastomeric jacket at least partly enclosing the pump, the elastomeric jacket being configured to define a flow channel having a first end arranged to receive air output by the pump outlet and a second end spaced apart from the first end for discharging the air output by the pump outlet following passage through the flow channel; a control unit for controlling operation of the mobile NPWT device; a battery arrangement for powering the mobile NPWT device; and a housing enclosing at least the pump, the elastomeric jacket, the control unit, and the battery arrangement.

The present invention is based on the realization that, particularly for a mobile NPWT device comprised in an NPWT system with continuous controlled leakage of air at the wound site, noise from the pump is one of the most important factors for user convenience and comfort. The present inventor has further realized that conventional silencers or mufflers are too bulky for use in a mobile NPWT device, and that good silencing can be achieved by at least partly enclosing the pump casing with an elastomeric jacket configured to define a flow channel for the air output by the pump.

Such an elastomeric jacket can provide the dual functionality of dampening noise caused by pump vibration, as well as acoustic noise carried by the air flow from the outlet of the pump. In addition to the dampening that can be achieved using, per se, known muffler principles through dimensioning of the flow channel, the material of the elastomeric jacket absorbs acoustic energy and contributes to the sound dampening.

In various embodiments, the elastomeric jacket may be configured in such a way that the flow channel is, at least partly, defined by the elastomeric jacket and the pump casing together. These embodiment may provide for a more compact solution and facilitated manufacturing of the elastomeric jacket.

An inside of the elastomeric jacket may advantageously be structured to have a first surface portion that is in contact with the pump casing and a second surface portion that is spaced apart from the pump casing, the second surface portion defining the flow channel together with the pump casing.

According to various embodiments, furthermore, a minimum cross-section area of the flow-channel may be smaller than a cross-section area of the pump outlet. Hereby, a controlled reduction of the pressure of the air output by the pump outlet can be provided for, which reduces the intensity of the noise. At least a portion of the flow-channel may exhibit a gradually increasing cross-sectional area.

The flow channel may extend at least 5 mm from the first end of the flow channel to the second end of the flow channel. Even more preferably, the flow channel may extend at least 10 mm, which would further reduce the tolerance requirements for the flow channel cross-sectional area, facilitating production of the elastomeric jacket.

The flow channel may extend along a non-straight path from the first end of the flow channel to the second end of the flow channel, preferably a meandering path. A non-straight configuration may provide for improved, more gradual pressure reduction by the flow channel.

According to various embodiments, the flow channel may have a first channel portion with a first maximum cross-section area adjacent to the first end of the flow channel, a second channel portion with a second maximum cross-section area adjacent to the second end of the flow channel, and a third channel portion between the first channel portion and the second channel portion, the third channel portion having a maximum cross-section area greater than the first cross-section area and the second cross-section area. In these embodiments, the expansion of compressed air output by the pump can be controlled to take place within a space defined the elastomeric jacket, which allows the elastomeric jacket to deform to absorb the energy carried by the compressed air, further contributing to dampening the noise from the pump.

In embodiments of the mobile NPWT device according to the present invention, the control unit may be configured to acquire a measure indicative of a supply voltage of the battery arrangement; and control, based on the acquired measure, a voltage provided to the pump towards a constant average voltage lower than the supply voltage.

It has been found that a factor contributing, in addition to sound dampening, to making the mobile NPWT more unobtrusive to the user is the consistency or invariability of the emitted sound. Emitted sound with varying frequency may be more noticeable than sound at a substantially constant frequency.

The NPWT device may include a pressure sensor arranged to sense a pressure in the canister. In such embodiments of the NPWT, it should be noted that the pressure sensor need not be arranged to directly sense the pressure in the canister, but that the pressure sensor may be arranged to sense the pressure at another location in the NPWT device, where the sensed pressure is indicative of the pressure in the canister. Furthermore, the pressure sensor may sense another property, such as force or deflection, based on which a change in pressure can be deduced.

The mobile NPWT device according to embodiments of the present invention may be included in a negative pressure wound therapy (NPWT) system, further comprising a chamber for establishment of a negative pressure, to be arranged at a wound site, the chamber having an outlet, and tubing flow connecting the outlet of the chamber and the inlet of the NPWT device.

In summary, the present invention thus relates to a mobile negative pressure wound therapy (NPWT) device, comprising an inlet; a canister in fluid flow connection with the inlet; a pump having a pump casing with a pump inlet in fluid flow connection with the canister for establishing a negative pressure in the canister, and a pump outlet for output of air transported through the pump; an elastomeric jacket at least partly enclosing the pump, the elastomeric jacket being configured to define a flow channel having a first end arranged to receive air output by the pump outlet and a second end spaced apart from the first end for discharging the air output by the pump outlet following passage through the flow channel; a control unit for controlling operation of the mobile NPWT device; a battery arrangement for powering the mobile NPWT device; and a housing enclosing at least the pump, the elastomeric jacket, the control unit, and the battery arrangement.

BRIEF DESCRIPTION OF THE DRAWINGS

These and other aspects of the present invention will now be described in more detail, with reference to the appended drawings showing example embodiments of the invention, wherein.

DETAILED DESCRIPTION OF EXAMPLE EMBODIMENTS

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Figure 1:
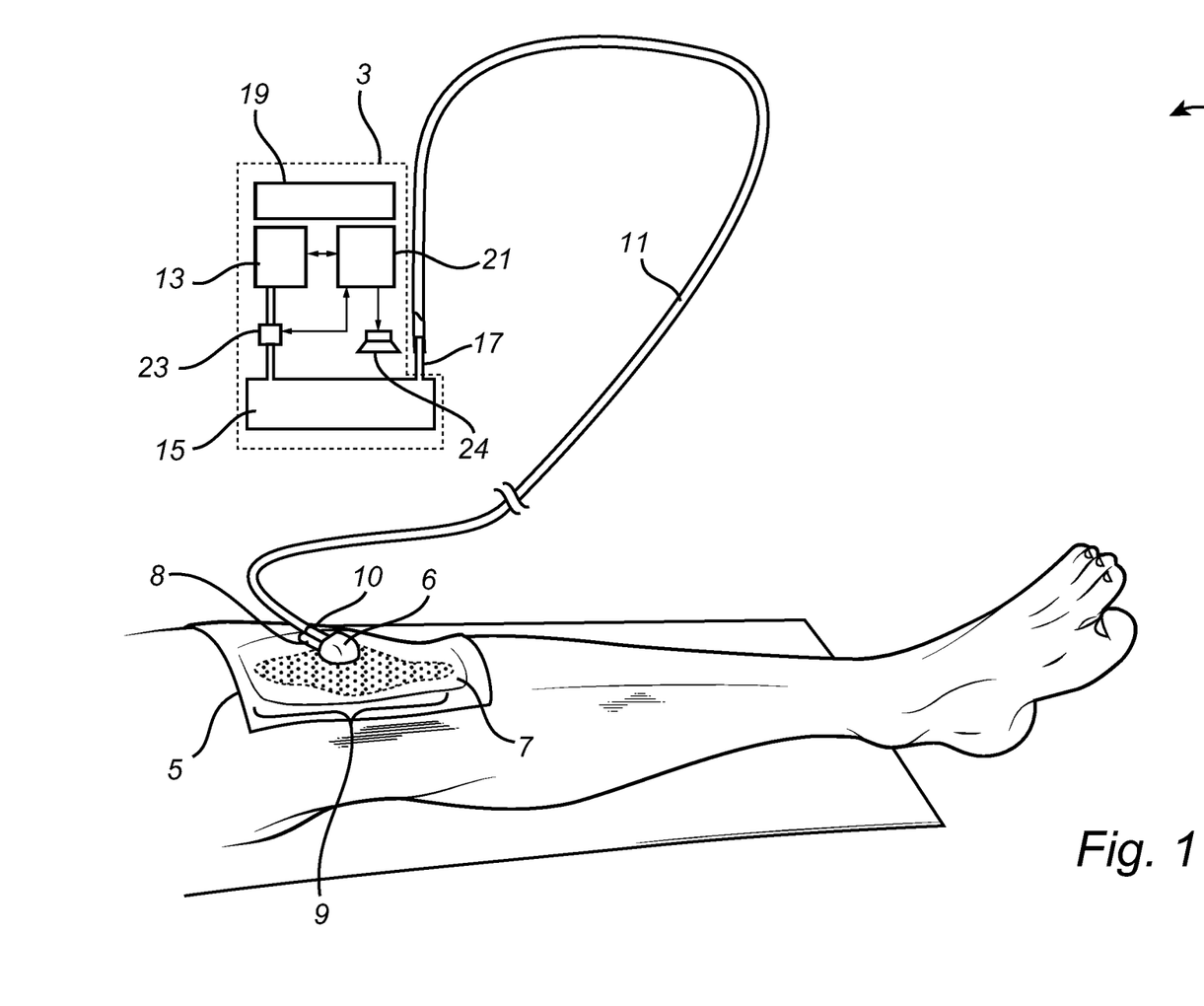
FIG. 1 is an illustration of an exemplary mobile NPWT system according to an embodiment of the present invention.

Turning now to the drawings and to FIG. 1 in particular, there is conceptually illustrated a negative pressure wound therapy (NPWT) system 1, comprising a mobile NPWT device 3 in accordance with an example embodiment of the present invention. The NPWT system 1 further comprises a wound cover 5 with a chamber 6 arranged at a wound site. The wound cover 5, including the chamber 6, is adapted to create a sealed space 7 defined in part by a wound surface 9, such as at the skin of a user, at or around a wound of the user. As is schematically shown in FIG. 1, the chamber 6 has an inlet 8 and an outlet 10. The outlet 10 of the chamber 6 is flow connected to the mobile NPWT device 3 using tubing 11, and the inlet 8 of the chamber 6 is in flow connection with an ambient (the air around the user) through a filter (not visible in FIG. 1) to provide for continuous leakage of air into the chamber 6. The tubing 11 may be any suitable flexible tubing fabricated from elastomeric and/or polymeric materials.

As is schematically shown in FIG. 1, the NPWT device 3 comprises a negative pressure pump 13 adapted for establishing a negative pressure when the negative pressure pump 13 is controlled to operate. The negative pressure pump 13 may be any type of pump that is biocompatible and maintains or draws adequate and therapeutic negative pressure levels. Preferably, the negative pressure level to be achieved may be in a range between about −20 mmHg and about −300 mmHg. In a possible embodiment of the present disclosure, a negative pressure range between about −80 mmHg and about −140 mmHg may be used. In a possible embodiment of the present invention, the negative pressure pump 13 is a pump of the diaphragmatic or peristaltic type.

The negative pressure pump 13 is fluid flow connected to a canister 15, the canister 15 also forming part of the NPWT device 3. The canister 15 may be formed from e.g. molded plastic or the like, and possibly being a detachable component of the NPWT device 3. The canister 15 may preferably be at least partly transparent/translucent to permit viewing into the interior of the canister 15 to assist the user in determining the remaining capacity of the canister 15.

An inlet port 17 is formed at the canister 15, for allowing connection to the tubing 11. The inlet port 17 may also be formed elsewhere at the NPWT device 3, however still fluidly connected to the canister 15. The connection between the inlet port 17 and the tubing 11 is a sealed connection, thus ensuring that no leakage is formed at the inlet port 17 during normal operation of the NPWT device 3. The tubing 11 is preferably releasably connected to the inlet port 17 through conventional means including a friction fit, bayonet coupling, snap fit, barbed connector, or the like. The inlet port 17 may be molded/formed from the same material and/or at the same time as forming the canister 15. A similar sealed connection (e.g. using a flange insulation/"O-ring") may be formed between the canister 15 and the negative pressure pump 13.

The NPWT device 3 further comprises a battery 19 for powering the NPWT device 3. The battery 19 may preferably be of the rechargeable type but may alternatively be disposable. A specifically adapted battery pack may be used in relation to some embodiments of the present disclosure.

The NPWT device 3 also comprises a control unit 21 for controlling operation of the mobile NPWT device 3, at least one pressure sensor 23 arranged to sense a pressure in the canister 15, and a speaker 24 for providing user feedback and/or alerts.

The control unit 21, which is powered by the battery 19 and coupled to the pump 13, the pressure sensor 23, and the speaker 24, may include a microprocessor, microcontroller, programmable digital signal processor or another programmable device. The control unit 21 may also, or instead, include an application specific integrated circuit, a programmable gate array or programmable array logic, a programmable logic device, or a digital signal processor. Where the control unit 21 includes a programmable device such as the microprocessor, microcontroller or programmable digital signal processor mentioned above, the processor may further include computer executable code that controls operation of the programmable device.

During use of the NPWT device 3, the wound cover 5 is arranged at a wound site of the user, forming the sealed space 7. The tubing 11 is provided to fluidly connect the outlet 10 of the chamber 6 in the wound cover 5 to the inlet port 17 of the NPWT device 3. To start the therapy, the mobile NPWT device 3 may then be activated, e.g. by the user, by pressing a start/pause button (not shown in FIG. 1). In response to this request to start the therapeutic treatment, the control unit 21 may control the negative pressure pump 13 to operate. When in operation, the negative pressure pump 13 will start to evacuate air through the canister 15, the inlet port 17, the tubing 11 and the sealed space 7 formed by the chamber 6 in the wound cover 5. Accordingly, negative pressure will be created within the sealed space 7. In case a liquid has been formed at the wound site, this liquid from the wound site may at least partly be "drawn" from the wound site, through the tubing 11, the inlet port 17 and into the canister 15 due to the continuous limited leakage provided by the inlet 8 of the chamber 6. The amount of liquid (sometimes referred to as exudate) that is drawn from the wound and collected in the canister will depend on the type of wound that is being treated as well as the type of wound dressing used. For example, in case an absorbent dressing is used, the liquid may be absorbed and collected both in the canister and the wound dressing, whereas if a dressing with no or little absorption capacity is used most or all of the liquid from the wound site may be collected in the canister. A suitable filter member (not shown in FIG. 1) may be arranged between the canister 15 and the negative pressure pump 13 to ensure that no liquid is allowed to pass to the negative pressure pump 13 from the canister 15.

Figure 2:
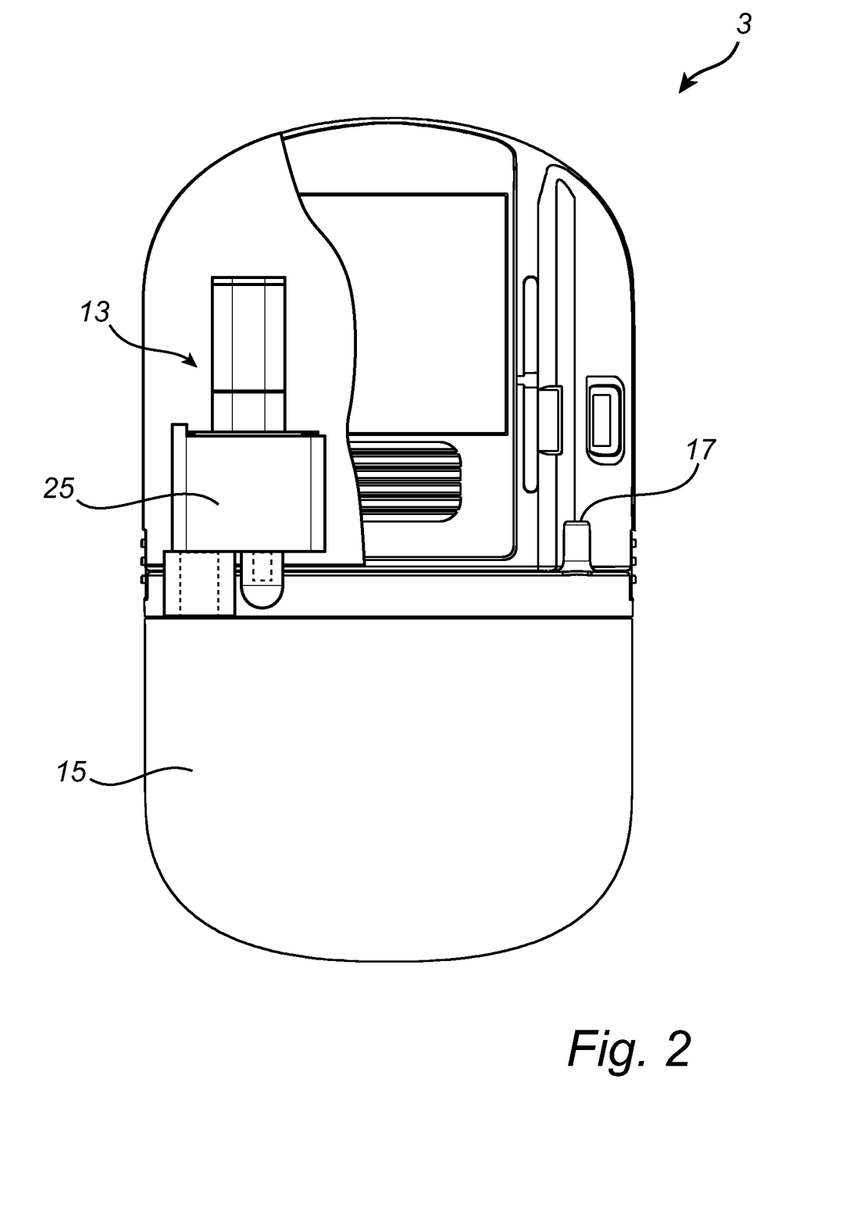
FIG. 2 is a side view of an NPWT device according to an example embodiment of the present invention, with a partly removed housing wall to show the pump and the elastomeric jacket.

FIG. 2 is a side view of an NPWT device 3 according to an example embodiment of the present invention. As was mentioned above with reference to FIG. 1, the NPWT device 3 comprises a pump 13. For noise suppression, the NPWT device 3 further comprises an elastomeric jacket 25 at least partly enclosing the pump 13. An example configuration of the elastomeric jacket 25, and its relation with the pump 13 will be described in greater detail below with reference to FIG. 3, and FIGS. 4A-B.

Figure 3:
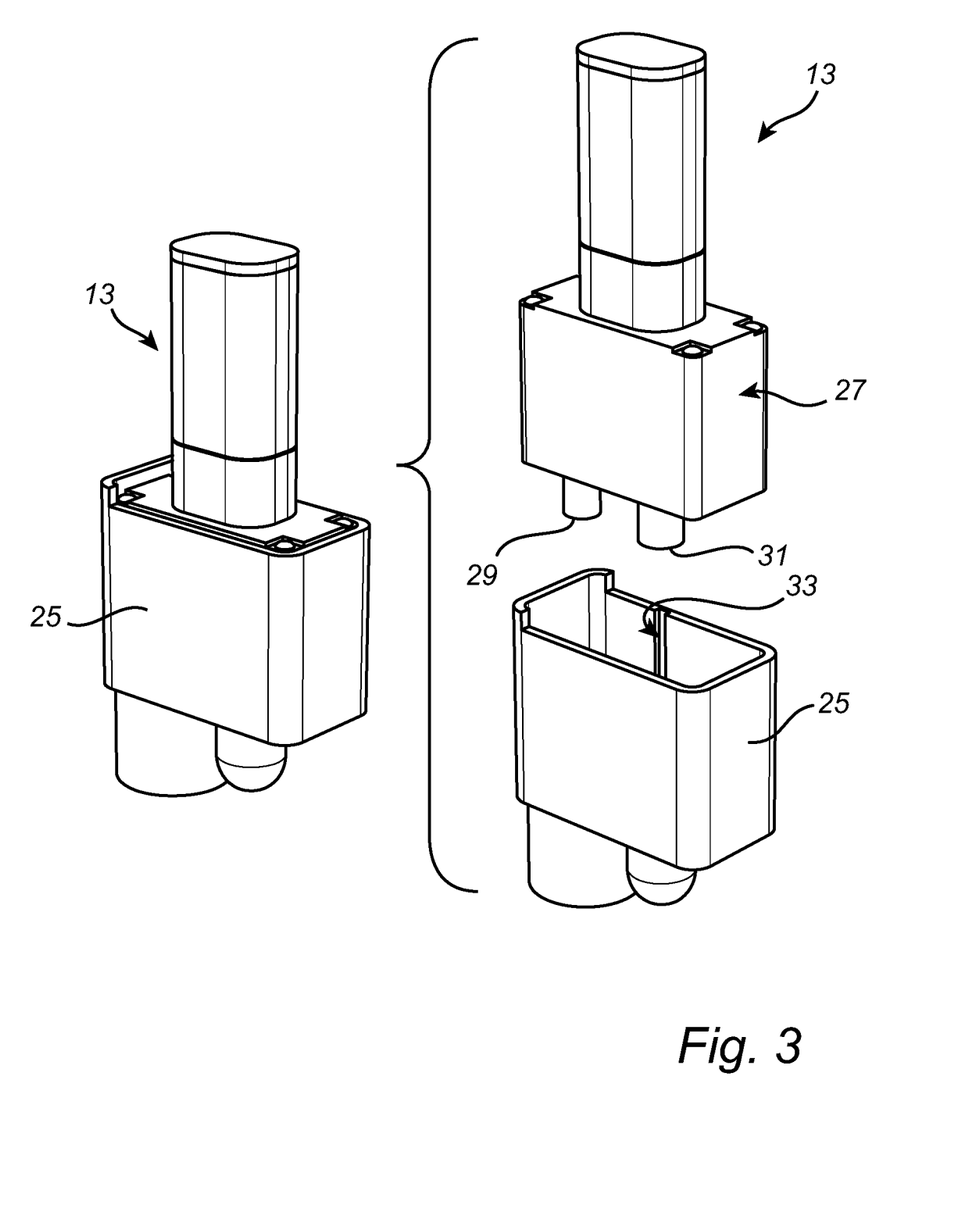
FIG. 3 is a perspective view of an example of the pump and elastomeric jacket comprised in the NPWT device in FIG. 2.

Turning first to FIG. 3, which is a perspective view of an example of the pump 13 and elastomeric jacket 25 comprised in the NPWT device 3 in FIG. 2, the pump 13 has a pump casing 27 with a pump inlet 29 and a pump outlet 31. As is schematically indicated in FIG. 2, the pump inlet 29 is in fluid flow connection with the canister 15 for establishing a negative pressure in the canister 15. Air transported through the pump 13 is output through the pump outlet 31.

As can be seen in FIG. 3, the elastomeric jacket 25 at least partly encloses the pump 13 and is configured to define a flow channel 33, that is partly visible in FIG. 3.

Figure 4A:
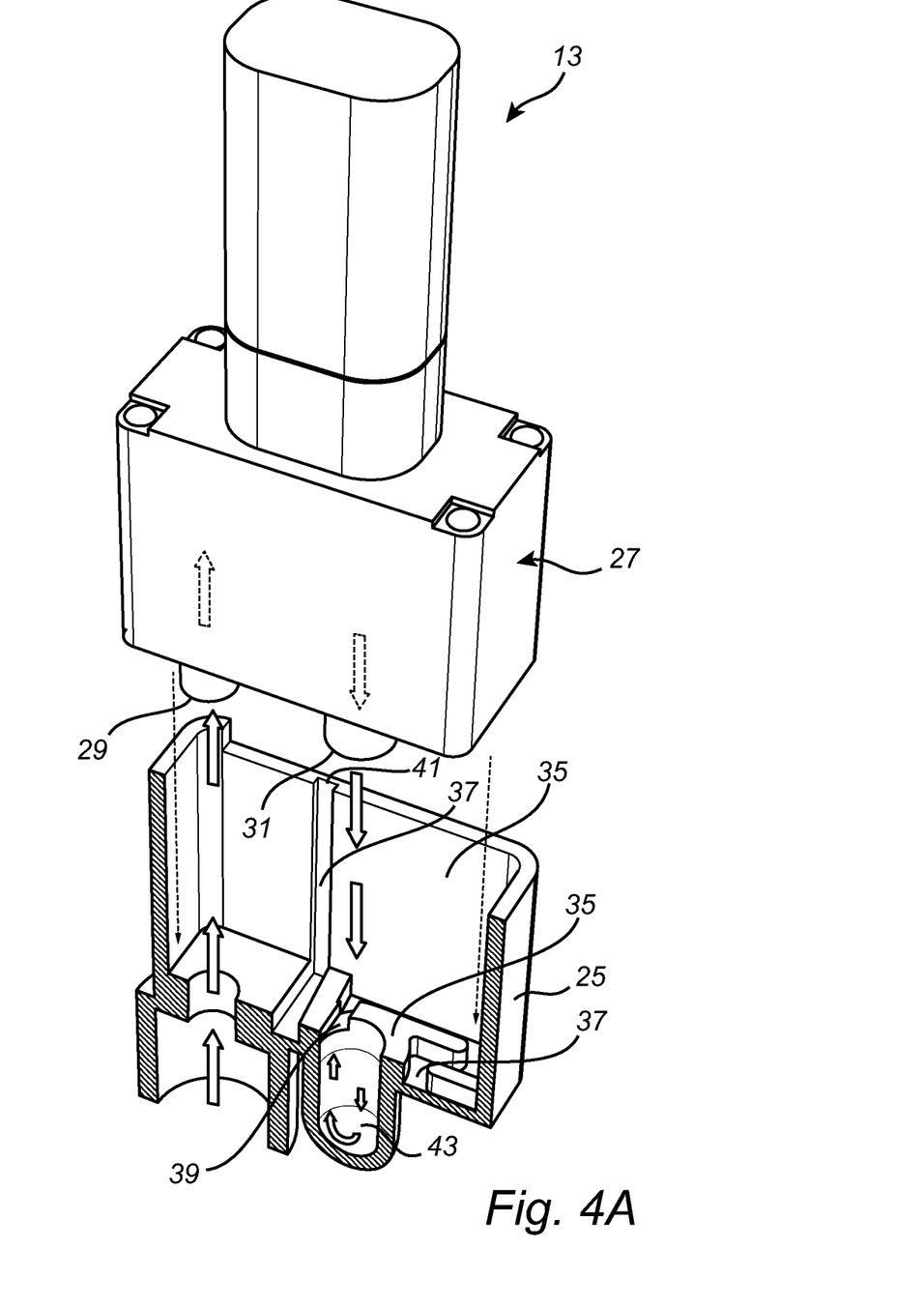
FIGS. 4A-B schematically show the air flow through the pump and the flow channel defined by the elastomeric jacket for an example configuration of the pump and elastomeric jacket.
Figure 4B:
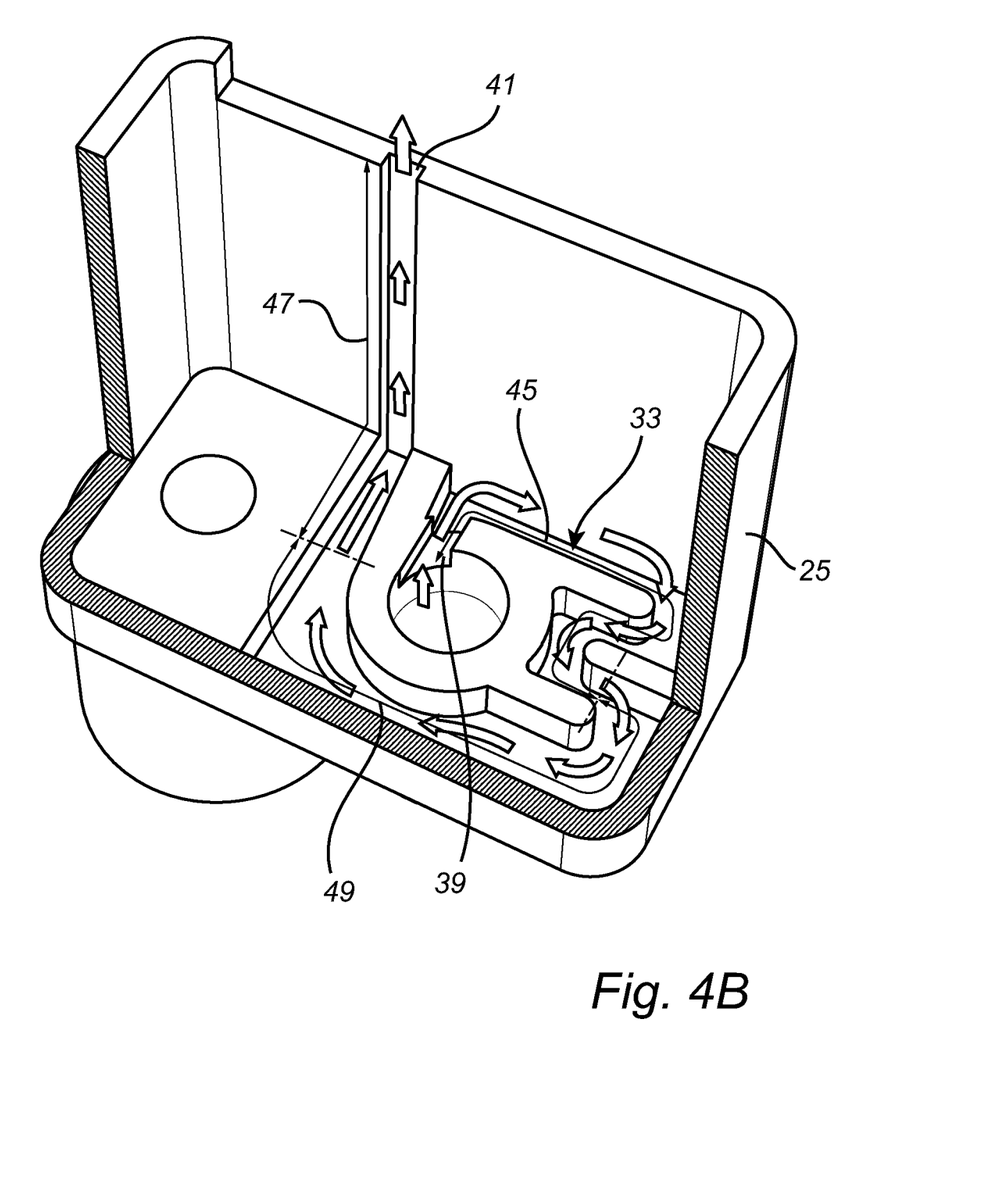

In the example configuration of FIG. 3 and FIGS. 4A-B, the pump casing 27 has substantially flat outer walls, and the flow channel 33 is defined by the elastomeric jacket 25 and the pump casing 27 together.

In particular, as may be best seen in FIG. 4A, an inside surface of the elastomeric jacket 25 is structured to have a first surface portion 35 that is in contact with the pump casing 27 and a second surface portion 37 that is spaced apart from the pump casing 27. The second surface portion 37 defines the flow channel 33 together with the casing 27.

In addition to illustrating an example configuration of the flow channel 33 defined by the elastomeric jacket 25, FIGS. 4A-B schematically show the air flow through the pump 13 and the flow channel 33 when the pump 13 is in operation. FIG. 4A shows a first part of the air flow, from the outlet of the canister 15 via the outlet 31 of the pump 13 to a first end 39 of the flow channel 33, and FIG. 4B shows a second part of the air flow, from the first end 39 of the flow channel 33 to a second end 41 of the flow channel 33.

Referring first to FIG. 4A, the pump 13 draws, when in operation, air indicated by block arrows in FIG. 4A from the outlet of the canister 15 (not shown in FIG. 4A) into the inlet 29 of the pump 13, to establish a negative pressure in the canister 15, as described above. The air is transported through the pump 13 using one of a number of, per se, known air transportation mechanisms and is output through the pump outlet 31. Connected to the pump outlet 31, the elastomeric jacket 25 comprises a generally dome shaped reservoir 43 for receiving and redirecting the air output through the pump outlet 31. As is schematically indicated in FIG. 4A, the reservoir 43 is fluid flow connected to the first end 39 of the flow channel 33.

Turning now to FIG. 4B, it can be seen how the flow channel 33 may extend along a non-straight path to guide the air output from the pump outlet 31 from the first end 39 to the second end 41 of the flow channel 33. For various kinds of suitable pump types 13, such as a diaphragm pump, air is not output at the pump outlet 31 in a steady flow, but in bursts of pressurized air. Along the flow channel 33, the air is first gradually depressurized, and then collected to be allowed to flow out through the second end 41 of the flow channel 33 as a more steady flow. Tests have shown that this results in a substantial reduction of the pump noise as perceived by the user.

To achieve this, the flow channel 33 may have a first channel portion 45 with a first maximum cross-section area adjacent to the first end 39 of the flow channel 33, a second channel portion 47 with a second maximum cross-section area adjacent to the second end 41 of the flow channel 33, and a third channel portion 49 between the first channel portion 45 and the second channel portion 47. The maximum cross-section area of the third channel portion is greater than the first maximum cross-section area of the first channel portion 45 and the second maximum cross-section area of the second channel portion 47. Advantageously, furthermore, the cross-section area of the first channel portion may be gradually increasing with increasing distance from the first end 39 of the flow channel 33, and the cross-section area of the second channel portion 47 may be gradually decreasing with decreasing distance to the second end 41 of the flow channel 33.

The flow channel 33 may extend at least 5 mm from the first end 39 to the second end 41, and it may be beneficial to design the flow channel 33 so that it extends at least 10 mm from the first end 39 to the second end 41. With a greater length of the flow channel 33, the tolerance requirements on the cross-section area (width and depth) of the flow channel 33 can be relaxed, which provides for simplified production, and more uniform performance.

Examples of suitable materials for the elastomeric jacket may include polyurethane, EPDM, and silicone rubber.

It should be noted that many other configurations of the flow channel 33 are possible. For instance, the flow channel may run internally in one or more walls of the elastomeric jacket 25. Other routings than the exemplary routing shown in FIG. 4B are also possible and may be beneficial depending on various factors, such as the kind of pump, the intended flow of air through the flow channel 33, and the general configuration of the NPWT device 3, etc.

It has been found that a factor contributing, in addition to sound dampening, to making the mobile NPWT more unobtrusive to the user is the consistency or invariability of the emitted sound. Emitted sound with varying frequency may be more noticeable than sound at a substantially constant frequency.

As the battery 19 becomes discharged, the battery voltage gradually decreases. Directly powering the pump 13 with the battery voltage would result in a corresponding change in the frequency of the sound emitted by the pump 13.

In order to eliminate or at least reduce such a change in the frequency of the sound emitted by the pump 13, the control unit 21 may be configured to acquire a measure indicative of a supply voltage of the battery 19; and to control, based on the acquired measure, a voltage provided to the pump 13 towards a constant average voltage lower than the supply voltage.

This may advantageously be achieved using, per se known, pulse width modulation, or other suitable techniques known in the art.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A mobile negative pressure wound therapy (NPWT) device, comprising:
   an inlet configured to be in fluid flow connection with a wound site;
   a canister in fluid flow connection with the inlet for collection of liquid from the wound site;
   a pump having a pump casing with a pump inlet in fluid flow connection with the canister for establishing a negative pressure in the canister, and a pump outlet for output of air transported through the pump;
   an elastomeric jacket at least partly enclosing the pump, the elastomeric jacket being configured to define a flow channel having a first end arranged to receive air output by the pump outlet and a second end spaced apart from the first end for discharging the air output by the pump outlet following passage through the flow channel, wherein the pump and elastomeric jacket cooperate to define a subassembly having an exterior, wherein the second end of the flow channel defines an outlet of the flow channel at the exterior of the subassembly, wherein the pump casing and elastomeric jacket each define respective portions of the outlet of the flow channel;
   a control unit for controlling operation of the mobile NPWT device;
   a battery arrangement for powering the mobile NPWT device; and
   a housing enclosing at least the pump, the elastomeric jacket, the control unit, and the battery arrangement.

2. The mobile NPWT device according to claim 1, wherein the flow channel is defined by the elastomeric jacket and the pump casing together.

3. The mobile NPWT device according to claim 2, wherein an inside of the elastomeric jacket is structured to have a first surface portion that is in contact with the pump casing and a second surface portion that is spaced apart from the pump casing, the second surface portion defining the flow channel together with the pump casing.

4. The mobile NPWT device according to claim 1, wherein a cross-section area of the flow-channel is smaller than a cross-section area of the pump outlet.

5. The mobile NPWT device according to claim 1, wherein the flow channel extends at least 5 mm from the first end of the flow channel to the second end of the flow channel.

6. The mobile NPWT device according to claim 1, wherein the flow channel extends along a non-straight path from the first end of the flow channel to the second end of the flow channel.

7. The mobile NPWT device according to claim 6, wherein the flow channel forms a meandering path from the first end of the flow channel to the second end of the flow channel.

8. The mobile NPWT device according to claim 1, wherein the flow channel has a first channel portion with a first maximum cross-section area of the first channel portion, the first maximum cross-section area adjacent to the first end of the flow channel, a second channel portion with a second maximum cross-section area of the second channel portion, the second maximum cross-section area adjacent to the second end of the flow channel, and a third channel portion between the first channel portion and the second channel portion, the third channel portion having a third maximum cross-section area of the third channel portion, wherein the third maximum cross-section area is greater than the first maximum cross-section area and the second maximum cross-section area.

9. The mobile NPWT device according to claim 1, wherein the elastomeric jacket is made of polyurethane, EPDM, or silicone rubber.

10. The mobile NPWT device according to claim 1, wherein the pump is a diaphragm pump.

11. The mobile NPWT device according to claim 1, wherein the control unit is configured to:
   acquire a measure indicative of a supply voltage of the battery arrangement; and
   control, based on the acquired measure, a voltage provided to the pump towards a constant average voltage lower than the supply voltage.

12. The mobile NPWT device according to claim 11, wherein the control unit is configured to control the voltage provided to the pump towards the constant average voltage using pulse width modulation.

13. A negative pressure wound therapy (NPWT) system, comprising:
   a chamber for establishment of a negative pressure, to be arranged at a wound site, the chamber having an outlet;
   the mobile NPWT device according to claim 1; and
   tubing fluidly connecting the outlet of the chamber and the inlet of the mobile NPWT device.

14. The NPWT system according to claim 13, wherein the chamber further has an inlet in flow connection with an ambient through a filter, to provide for continuous leakage of air into the chamber.

\* \* \* \* \*